United States Patent [19]

Hedberg

[11] Patent Number: 4,865,586
[45] Date of Patent: Sep. 12, 1989

[54] SUCTION STYLET FOR ENDOTRACHEAL INTUBATION

[76] Inventor: Martha Hedberg, 4279 Crooks Rd., Royal Oak, Mich. 48073

[21] Appl. No.: 239,024

[22] Filed: Aug. 29, 1988

Related U.S. Application Data

[63] Continuation of Ser. No. 99,664, Sep. 21, 1987, abandoned, which is a continuation of Ser. No. 864,521, May 19, 1987, abandoned.

[51] Int. Cl.⁴ .............................................. A01M 11/00
[52] U.S. Cl. ..................................... 604/93; 604/281; 128/207.14
[58] Field of Search ................... 604/54, 49, 286–288, 604/46, 35, 93, 43, 45, 118, 119, 164, 170, 283, 284, 285; 128/207.14, 207.15, 656–658

[56] References Cited

U.S. PATENT DOCUMENTS

| | | | |
|---|---|---|---|
| 2,862,998 | 12/1958 | Weekes | 604/280 |
| 2,912,982 | 11/1959 | Barsky | 128/207.14 |
| 3,043,309 | 7/1962 | McCarthy | 604/54 |
| 3,322,126 | 5/1967 | Rusch et al. | 604/280 |
| 3,734,094 | 5/1973 | Calinoy | 128/207.15 |
| 3,811,149 | 5/1974 | Gravelee et al. | 604/280 |
| 4,244,362 | 1/1981 | Anderson | 128/207.14 |
| 4,275,724 | 6/1981 | Behrstock | 604/164 |
| 4,300,550 | 11/1981 | Gandi et al. | 604/35 |
| 4,364,394 | 12/1982 | Wilkinson | 604/35 |
| 4,502,482 | 3/1985 | Deluccia | 604/170 |
| 4,571,239 | 2/1986 | Heyman | 604/54 |
| 4,607,635 | 8/1986 | Heyden | 604/35 |

FOREIGN PATENT DOCUMENTS

| | | | |
|---|---|---|---|
| 2140755 | 4/1981 | Fed. Rep. of Germany | 604/280 |
| 3323482 | 6/1984 | Fed. Rep. of Germany | 604/280 |

OTHER PUBLICATIONS

"For-Clear Plastic Tubes", Foregger Hospital Catalogue, Apr. 23, 1975.

Primary Examiner—Max Hindenburg
Assistant Examiner—K. M. Reichle
Attorney, Agent, or Firm—Lynn E. Cargill

[57] ABSTRACT

This invention pertains to a suction guide for endotracheal intubation stylet having a first portion made of substantially rigid material having a tubular shape with a plurality of openings for suctioning unwanted fluids therethrough, a second portion integral with and immediately adjacent to the first portion, being made of a semi-rigid material, said second portion having a tubular shape and a sufficient length to be bent and inserted into a human body cavity, and a third portion integral with and immediately adjacent to the second portion, being made of a flexible material having a tubular shape and of a sufficient length to extend from a body after insertion with an open end adapted for connection to a suction source. The second portion is semi-rigid and is inserted into the tracheal passage through the throat of the patient and acts as a guide for subsequent insertion of an endotracheal tube over the stylet.

1 Claim, 1 Drawing Sheet

SUCTION STYLET FOR ENDOTRACHEAL INTUBATION

This is a continuation of application Ser. No. 099,664 filed on Sept. 21, 1987, now abandoned, which is a continuation of application Ser. No. 864,521 filed on May 19, 1987, now abandoned.

TECHNICAL FIELD

The present invention relates generally to a medical device insertion guide stylet and suction catheter, and more specifically to an endotracheal intubation stylet and suction catheter combination.

BACKGROUND OF THE INVENTION

The insertion of tubular medical devices into human bodies has always presented problems. Forcing tubes through a convoluted path to reach various body organs is difficult in a surgical setting while the patient is sedated and prepared for the insertion.

However, on many occasions the necessity for intubation arises during an emergency when the patient is in an hypoxic or other distressed condition. Because the personnel of emergency rooms and rescue vehicles are not expert at the insertion of intubation tubes into the trachea, the intubation tube may be misplaced in the esophagus, or may cause trauma to tissue. In the instance of an attempted endotracheal intubation, a common complication during intubation in the insertion of the intubation tube into the esophagus rather than the tracheal passage. If this mistake has been made, and pressurized air in forced through the endotracheal tube down the esophagus, the contents of the stomach are forced back up and may enter the lungs, doing severe damage to the tissue.

To perform an oral intubation, a laryngoscope is generally used to provide the operator with a view of the vocal cords. The intubation tube must be curved anteriorly through the vocal cords and inserted into the trachea. Because this is such a precise operation, it is preferable that the patient be absolutely still. This is nearly impossible, considering the patient will probably experience a retch response to the oral insertion of the laryngoscope. Further complications occur among patients who have a deformity of the neck or throat or other conditions such as diseased tissue which would impede the insertion of something down the throat. For such patients, intubation under ideal conditions is difficult at best. Under emergency conditions, such as cardiopulmonary resuscitation it is difficult to perform an intubation because the patient is jostled, rendering the larynx a moving target. In such situations, it is imperative to have a method of insertion for the intubation tube which is quick, reliable, and effective.

During emergency circumstances, such as cardiopulmonary resuscitation, fluid such as mucus or vomitus, may be present in the tracheal passage due to ventilation. Ventilation is accomplished with a mask and a bag to squeeze air into the lungs. As the mask is placed over the nose and mouth, both the lungs and the stomach are inflated and the fluids in both those body cavities are displaced. The situation further departs from the ideal controlled intubation because in an emergency the patient is usually hypoxic at the outset.

During cardiopulmonary resuscitation, the intubation may be attempted several times, and those efforts interrupted with bag and mask ventilation to provide much needed oxygen to the patient. At this point, there are two objectives for the operator of the intubation to achieve:

1. clearing the oropharynx of secretions so that the operator can see the vocal cords; and
2. intubating into the trachea as quickly as possible between the vocal cords.

If too long an interval passes without success during attempted intubation, mask and bag ventilation must be resumed before intubation is attempted once again. Generally, a human brain will endure about five minutes of an anoxic state before brain damage begins. Therefore, this entire operation must be performed speedily and with a high degree of accuracy. As emergency personnel are not necessarily experts at intubation, a method is needed to provide speedy, reliable and effective insertion of an intubation tube to supply oxygen to the lungs.

In a second situation, the lungs of a patient may require suctioning of copious secretions which the patients cannot clear effectively by coughing. Conventionally, these patients have a soft catheter inserted intranasally, but this is uncomfortable and may cause trauma to tissues. The same problem as described before arises because entry into the tracheal passage is not assured. Current alternatives to this practice include the insertion of a nasopharyngeal airway, which is left in place in the nostril. This method spares the patient the discomfort of constant removal and insertion of a catheter, but the problem of inserting the catheter into the trachea remains.

Additionally, it would be advantageous to have a disposable medical device which could selectively suction either main stem bronchus of the lung for sample taking purposes. The problem arises from the inability to precisely insert a suctioning device into a selected body cavity.

And yet a further problem is presented when specimens of fluid must be removed from the lungs when a patient is suspected to have pneumonia. Immediate microscopy and staining may suggest antibiotics to be administered to prevent further damage to the lungs of the patient. Traditionally, if a patient could not produce a specimen by coughing, he was given a mist to breathe to loosen the secretions prior to repetition of the coughing action. Conventional soft nasal suction catheters may be attached to a sputum trap. An attachment, the suction stylet, fitted to a sputum trap for withdrawing specimens discharged from the surface of respiratory passages would permit effective specimen-taking for problem patients.

An endotracheal tube, as disclosed in U.S. Pat. No. 4,063,561 issued on Dec. 20, 1977, includes therein metallic material within the walls of the tube to be influenced by external magnetic devices placed over the larynx of the patient externally. Because the trachea is anterior to the esophagus in a patient, the tip of the endotracheal tube is to be drawn by the external magnetic device into line with the trachea and inserted therein.

Another endotracheal control device as disclosed in U.S. Pat. No. 4,244,362 issued on Jan. 13, 1981, goes further by disclosing a first magnetic means attached to one end of the stylet and a second magnetic means for external placement over the tracheal orifice of a patient. The first magnetic means is reusable.

SUMMARY OF THE INVENTION

Accordingly, it is an object of the present invention to provide a guide for an endotracheal tube which is adapted to receive the endotracheal tube sleeved thereover permitting positioning of the tube within a human body. The guide is adapted to permit suctioning of mucus as well as providing guidance during the insertion process. This dual function permits an operator to position the guide more easily than an endotracheal tube itself. The ability to suction enables an operator to clear obstructing mucus from the visual path, thereby facilitating insertion of the guide into the proper place. Removal of the guide may be performed as soon as it has served its purpose, namely, to direct the introduction of the endotracheal tube through the larynx into the trachea for the purpose of providing a patent airway in a patient by receiving the endotracheal tube thereover.

In the invention, the stylet guide comprises a first portion made of substantially rigid material having a tubular shape terminating in a tip with a plurality of openings for suctioning unwanted fluids therethrough, said rigid material being of a composition which remains patent during suctioning, a second portion which is integral with and immediately adjacent to the first portion and a third portion integral with and immediately adjacent to the second portion.

The second portion is made of a semi-rigid material which may be shaped by an operator to approximate the curvature of the oropharynx of the patient. The second portion has a round tubular shape and a sufficient length to be bent and inserted so as to submerge the first portion into unwanted fluids to be removed. The second portion is further adapted to receive the endotracheal tube sleeved thereover to permit positioning of the tube within the body cavity. The semi-rigid material of the second portion is of a sufficient rigidity to maintain the curvature as shaped by the operator so as to form a guide for the endotracheal tube and remain patent during suctioning.

The third portion of the suction stylet guide is made of a flexible material, has a round tubular shape, and includes an open-end adapted for connection to a suction source.

The first, second and third portions all have an outer diameter no greater than one-half the inner diameter of the endotracheal tube so as to allow sleeving of the endotracheal tube thereover. The flexible material of the third portion is also of such a composition as to remain patent during suctioning.

The suction stylet guide for endotracheal intubation of the present invention provides a means for easily and speedily inserting a large, cumbersome endotracheal tube into a patient within a short period of time. After the endotracheal tube has been sleeved over the guide and is in position within the patient, the suction stylet guide may be extracted, leaving the endotracheal tube in place in the trachea. This will curtail unnecessary trauma to tissue and will facilitate emergency room procedures.

DETAILED DESCRIPTION OF THE INVENTION

Figure 1:
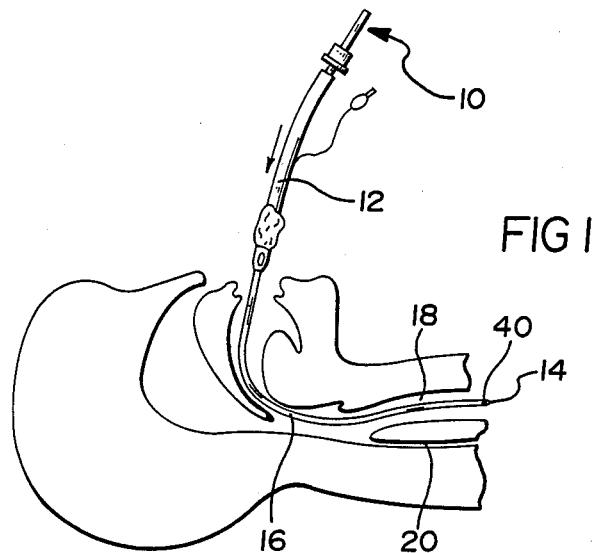
FIG. 1 is a view of the suction stylet guide of the invention in position in the patient.

Looking now to the drawings, FIG. 1 illustrates the use of the invention when intubation is practiced orally. FIG. 1 shows suction stylet 10 introduced into the tracheal passage of a patient through the throat. As illustrated, the suction stylet 10 will be positioned to act as a guide for the insertion of an endotracheal tube 12 into the trachea 18. First portion 14 of suction stylet 10 has therein a plurality of openings 40 for suctioning fluids from the throat and trachea. A second portion 16 of suction stylet 10 may be bent to approximate the curvature of the oropharynx of the patient. Once second portion 16 is bent, the tip of first portion 14 may be aimed at the opening of the trachea and the entry into the trachea may be observed. The remainder of the suction stylet 10 will follow the tracheal passage, rather than tending to enter esophagus 20. Endotracheal tube 12 is then sleeved over stylet 10 to place the endotracheal tube in position inside tracheal passage 18, rather than in esophagus 20. Suction stylet 10 may then be withdrawn from endotracheal tube 12, leaving the endotracheal tube in position inside tracheal passage 18.

Figure 2:
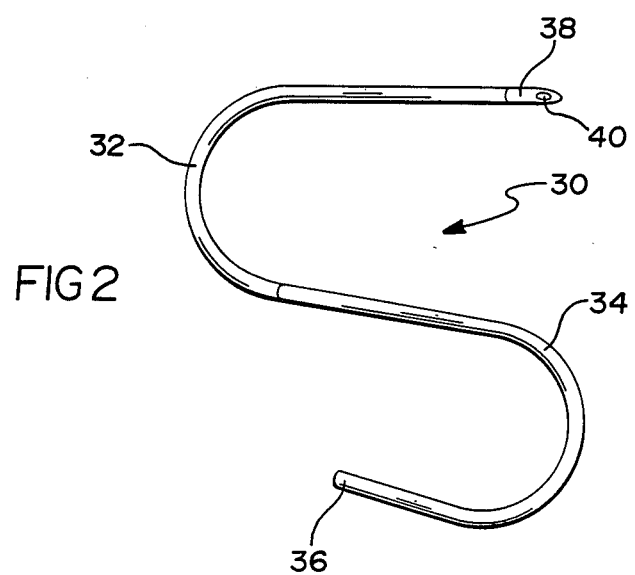
FIG. 2 is a plan view of one embodiment of the suction stylet of the invention.

FIG. 2 illustrates a suction stylet as constructed in accordance with the present invention. The suction stylet is generally indicated by numeral 30, having a first portion 38, a second portion 32, and a third portion 34. The first portion 38 is about one quarter inch to one and one half inches in length and is introduced into a patient orally after the second portion has been bent to approximate the curvature of the oropharynx in the patient. First portion 38 has a plurality of openings 40 for suctioning unwanted fluids from the throat and endotracheal passage. Second portion 32 is about three inches to six feet in length and is made of a material such as a memory plastic material, or other disposable material which will maintain a curvature after bending similar to that of the oropharynx or bronchi. Alternatively, the material could also be manufactured so that it may be stiffened to maintain curvature by the embedding or implantation of wires within the walls of the suction stylet. Any other conventional means may be employed to stiffen the tubular material used for suction stylet 30 to maintain a curvature after the stylet has been bent.

Referring again to FIG. 2, third portion 34 is located between second portion 32 and an open end 36. Third portion 34 has a sufficient length for an endotracheal tube to be sleeved over it, such that its end 36 is able to be attached to a suction source while leaving sufficient length for the operator's hand or fingers to manipulate the stylet portion simultaneously. Depending upon the application, third portion 34 is preferably from 6 inches to 10 feet in length. In application to a human patient, the preferable length is approximately 3 feet. Concerning animal applications, the preferable length is determined by the size of the animal. Third, portion 34 is preferably translucent to enable the operator to see the amount and quantity of fluids being suctioned therethrough. The surface of the stylet 30 preferably has a surface which will facilitate the sleeving of an endotracheal tube over the suction stylet.

Referring once again to FIG. 2, end 36 is adapted for coupling with a detachable suction port. End 36 should be made of a sufficiently rigid material such that it will not be compressed or kinked by the suction port adapter, as kinking would impair suctioning. An inserted suction port adapter should not be able to significantly enlarge end 36 such that an endotracheal tube could not be easily sleeved over it after the suction port adapter has been detached. The outer diameter of end 36 should preferably be no greater than one half the inner diameter of an appropriately sized endotracheal tube. This will prevent the suction port from entering the endotracheal tube. The preferable detachable suction port may be a sponge lock means which is connectable to a suction source.

Figure 3:
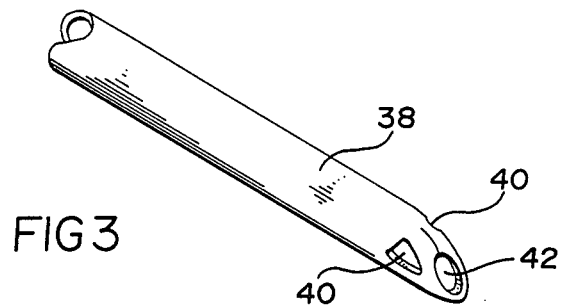
FIG. 3 is a perspective view of the end portion of the suction stylet.

Referring now to FIG. 3, first portion 38 is illustrated in greater detail. A plurality of openings 40 are shown in their preferable configuration. Lumen 42 is located at the tip of first portion 38, while side openings 40 are located in a position which would allow the suctioning of fluids in the event that lumen 42 is blocked by tissue. Having a plurality of openings substantially prevents any blockage by providing more than one route for unwanted fluids to be suctioned therethrough. Preferably, more than one side opening 40 will be present.

A method for endotracheal intubation of a patient using a suction stylet incorporating a suction catheter includes bending a foresection of the stylet and inserting the stylet through the vocal cords. The suction stylet is bent to approximate the curvature of the oropharynx and bronchi of the patient being intubated. Bending the suction stylet in this manner eases insertion of the stylet into the tracheal passage, avoiding insertion into the esophagal passage. An endotracheal tube can then be sleeved over the suction stylet and guided into the tracheal passage. The suction stylet may be connected to a suction source to remove unwanted fluids from the tracheal passage. Insertion of the suction stylet through the vocal cords may be accomplished by conventional laryngoscopy and oral insertion.

While the best modes have been described in detail, those familiar with the art to which this invention relates will recognize various alternative compositions and methods for practicing the invention as defined by the following claims.

What is claimed is:

1. A suction stylet guide adapted to be connected to a suction source for endotracheal intubation of a patient, comprising:

a first portion made of a substantially rigid material having a round tubular shape terminating in a tip with a plurality of openings for permitting suction of unwanted fluids therethrough, said first portion being from about one-quarter to one inch in length;

a second portion unitary and coaxial with the first portion, said second portion being made of a semi-rigid bendable memory material which will permit shaping to and maintaining of a curvature approximately the curvature of the oropharynx of the patient, said second portion having a round tubular shape and being from about 3–6 inches in length permitting insertion into the patient so as to submerge said first portion into unwanted fluids to be suctioned, said second portion being adapted to receive a round endotracheal tube sleeved thereover permitting positioning of the tube within the patient;

a third portion unitary and coaxial with the second portion, said third portion being made of a flexible material, said third portion having a round tubular shape, an open end adapted for connection to the suction source, and being from about six inches to five feet in length;

said first, second and third portions being sized to allow sleeving of the endotracheal tube over the suction stylet guide; and said open end of the third portion adapted to receive a detachable suction port means that is hand-operated and non-integral with said suction stylet guide.

* * * * *